United States Patent [19]

Christensen

[11] Patent Number: 4,704,104
[45] Date of Patent: Nov. 3, 1987

[54] DISPOSABLE TUBE FOR RECTAL INJECTION OF DRUGS

[76] Inventor: John F. Christensen, Åboulevard 50[5], Copenhagen N, Denmark, DK-2200

[21] Appl. No.: 841,586

[22] Filed: Mar. 20, 1986

[51] Int. Cl.[4] .............................................. A61M 5/24
[52] U.S. Cl. .................................... 604/205; 604/216
[58] Field of Search ............ 604/205, 204, 216, 89–91, 604/57, 236, 237, 238, 264, 271, 416

[56] References Cited

U.S. PATENT DOCUMENTS

| | | | |
|---|---|---|---|
| 2,176,923 | 10/1939 | Nitardy | 604/416 X |
| 2,636,493 | 4/1953 | Lockhart | 604/90 |
| 2,717,598 | 9/1955 | Krasno | 604/216 |
| 3,512,524 | 5/1970 | Drewe | 604/204 X |
| 3,835,855 | 9/1974 | Barr, Jr. | 604/89 |
| 4,020,836 | 5/1977 | Cunningham | 604/204 |

Primary Examiner—John D. Yasko
Attorney, Agent, or Firm—Thomas R. Morrison

[57] ABSTRACT

A disposable tube includes two compartments separated by a breakable partition. One of the compartments initially contains one element of a medicament, the other compartment initially contains a second element of the medicament. The first compartment, includes a bellows, maintained compressed in its initial condition. The partition is breakable whereby the first and second elements are mixed together. The bellows is expandable from its initial condition whereby the second element is drawn into the first compartment for mixing the first and second elements together. A hollow tip permits evacuating the interior of the first and second compartments for administration of the mixture.

4 Claims, 2 Drawing Figures

DISPOSABLE TUBE FOR RECTAL INJECTION OF DRUGS

This invention relates to a disposable tube for rectal injection of medicaments. Till now such tubes have mainly been used for injecting an apportioned quantity of a laxative. Contrary to tubes intended for cosmetics or paints and glue and having a short neck, which is closed by a screw-cap, then syringe-tubes have a comparatively long neck making it possible to conduct the medicament high enough up to act on the colon.

Except for laxatives, medicaments to be administered by the patient himself, e.g. pain-stilling remedies or antibiotics, till now have been given in the form of pills, while e.g. stronger and quick action analgesics are injected by means of hypodermic needles and are administered by experts. Pills which are swallowed must pass the stomach and this has at best a delaying effect as an absorption at the earliest takes place in the intestinal canal, and at worst they have such an irritating effect on the stomach that they may lead to a gastric catarrh or even to vomiting.

Therefore there exists a requirement for medicaments which can be given rectally. Such do exist. E.g. there are analgesics available which are meant for rectal injection in a liquid state, but these are not stable in their ready condition, and consequently they are supplied in the form of a powder and a dissolvent which will be mixed immediately before they are injected. Therefore, syringe-tubes as above are not applicable, as it is unpredictable how long a time will elapse from the charging and weld-closing of the tube till it is emptied by a user.

There exist tubes divided into two chambers by a partition, said tubes being intended for containing a drug component each, e.g. a powder and a solvent, which must not be mixed till immediately before use. Precedents of such tubes are for instance described in U.S. Pat. No. 2,176,923. The tube described therein is divided into two chambers by a dividing wall having weakening lines or thin areas, so that said wall is broken by pressure thus allowing a liquid to flow from one chamber into the other. Another example of such tubes are described in U.S. Pat. No. 3,347,410 which deals with a double-walled tube. A barrage membrane between the walls can be perforated by a tack attached to a bellows-shaped tube neck, so that said tack penetrates the membrane when the tube neck is compressed.

Such tubes are not very suitable for rectal injection of drugs to be mixed in the tube when the injection must be carried out by the user himself/herself.

In order to obtain a swift and safe dissolution of the powdered drug component, the greater part of the solvent must be conducted to the chamber containing the powder, which implies that the two chambers must have almost the same volume. This increased volume alone makes the tube unwieldy for the user, but add to this that a partition placed in the middle of the tube-casing makes it difficult to have a sufficient emptying of the tube when it is squeezed together. An insufficient emptying not only mean loss of some medicament, but also a doubtful dosing of the latter.

It is the aim of this invention to manufacture a disposable tube for rectal injection of the above sort, being divided into two chambers by a partition and having means to break the partition wall and not taking up more space than would a tube containing the ready-mixed drug, without making it more complicated to use it than anybody being able to manage.

According to the invention this is obtained by the fact that the section of the tube-casing reaching from the partition wall to the tip of the tube is shaped as an extractable bellows.

In its normal state, i.e. when the tube is delivered charged with drug and dissolvent, and when injection is carried out, the bellows is compressed. When the medicament is going to be ready-mixed the partition wall is perforated in a well-known way, either bursting it by a strong pressure on the tube or perforating it with a pointed rod which is put down through the tip of the tube, after which the bellows is drawn or pressed out thus providing so much space that all of or nearly all of the dissolvent can be contained. When the drug is dissolved the bellows-shaped part of the casing can be compressed again and the injection be carried out just as easily and conveniently as with a normal one-chamber tube made for rectal injection.

In order to make it possible to fill the tube in the usual way through its not yet closed and sealed end, according to an embodiment of the invention the dividing wall may be constituted of the bottom of a tubular insert, which when the powdered drug has been charged is inserted into the tube to bear against the bellows-shaped part of said tube. When the dissolvent has been charged, the closing of the tube can be done in the usual way, viz. by simultaneously welding the insert and the tube-case along the compressed bottom edge.

Below the invention will be further described with reference to the accompanying drawing, in which.

Figure 1:
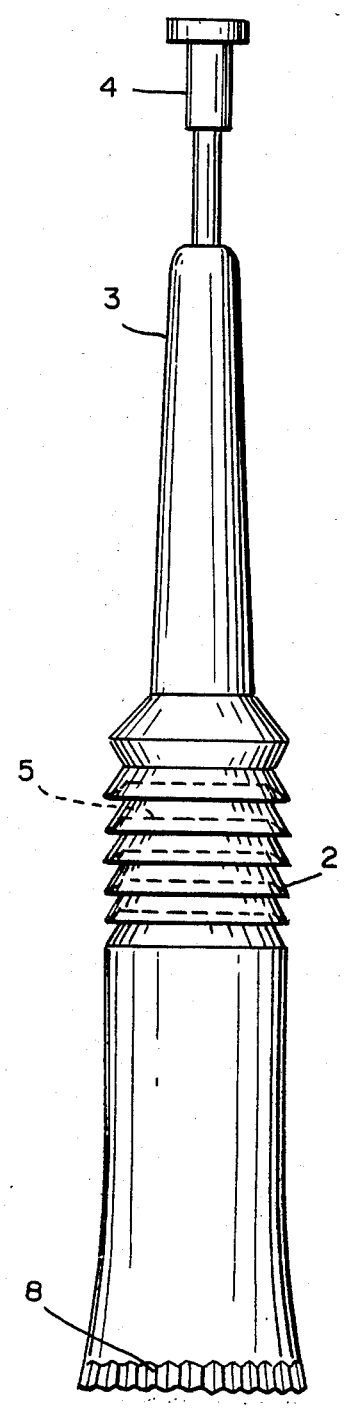
FIG. 1 shows an embodiment of a tube according to the invention.
Figure 2:
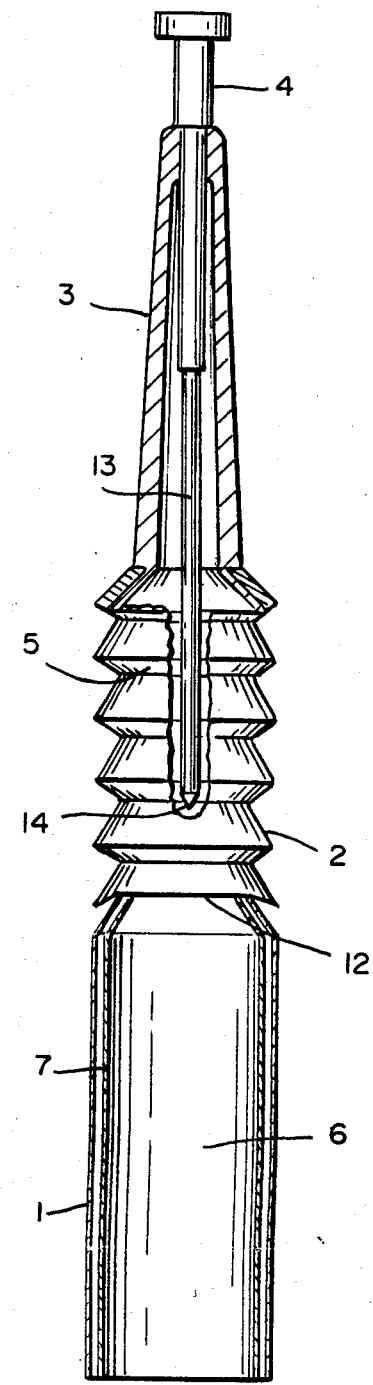
FIG. 2 is a sectional view of the same tube.

The tube shown in the drawing consists of a thin-walled case 1, the top of which is shaped as an extractable bellows 2. In FIG. 2 the bellows 2 is shown in its extracted state. The tube has a hollow tip 3 of which the exterior is slightly conical, and until it is used said tip is closed by e.g. a pressed-on cap, or as shown in the drawing by a rod-shaped plug 4 which has an extension 13 ending in a point 14. By a partition 12 the case 1 is divided into two compartments 5 and 6; the compartment 5 which is constituted of the extractable part of the case is designed to contain the powdered drug, whereas the compartment 6 is intended for containing a solvent. As it appears from FIG. 2 the partition 12 is made up of the bottom section of a tubular, thin-walled insert 7 which, when the powdered drug has been charged, is inserted into the smooth part of the case 1, and, when filled with the solvent, it is welded together with the case along its bottom edge as shown in FIG. 1.

As it is known from the previously mentioned U.S. Pat. No. 2,176,923, the bottom 12 of the casing 7 may have weakenings making it burst at a strong pressure. A simpler, and a fully as reliable design is obtained by providing the tube with a rod-shaped plug 4 as it is shown in the drawing. FIG. 1 shows the plug partially drawn out, so that its point 14 does not touch the dividing wall 12. If the plug is pushed the whole way down, as shown in FIG. 2, but before extraction of the bellows-shaped section 2 of the case, then said point 14 of the rod 13 will perforate the partition wall 12, so that the solvent in compartment 6, when the case section 2 has been extracted, can be squeezed up into the now profusely enlarged compartment 5, and the powder be dissolved by shaking the tube. When the tube has been pressed back to its original size and the plug 4 has been pulled out, the tube is ready for injection.

In FIG. 2 the insert 7 is shown having a diameter slightly smaller than the interior diameter of the tube case. In fact the insert fits tightly into the tube case. As it appears from the same figure the bottom of the insert 12 may be arched upwards or shaped as a truncated cone. This gives the bottom a certain rigidity.

As it will appear from the above explanation the partition 12 is fairly near the tube's tip 3 when the tube is in its compressed state (FIG. 1), whether said partition wall in a well-known manner is directly attached to the tube case or is the bottom of an insert as in the embodiment shown, and therefore it will not impede the compression of the tube.

I claim:

1. A disposable tube for administering a medicament, comprising:
   a case;
   a partition in said case dividing said case into first and second compartments;
   said first compartment including a bellows;
   said first compartment having a capacity, when said bellows is contracted, effective for containing a first component of said medicament;
   said second compartment having a capacity for containing a second component of said medicament;
   means for puncturing said partition, whereby said first and second compartments may be placed in communication with each other;
   said first compartment having a capacity, when said bellows is expanded, for containing substantially all of said first and second components, whereby said first and second components may be mixed together; and
   a hollow tip communicating with at least one of said first and second compartments, whereby a mixture of said first and second components may be administered.

2. A disposable tube according to claim 1, wherein said second compartment includes an insert within said casing, said partition being integral with said insert, and said insert being sealed within said casing.

3. A disposable tube according to claim 1 wherein said means for puncturing includes:
   a plug insertable in said hollow tip;
   an extension on said plug;
   a point on said extension; and
   means for permitting said point to puncture said partition.

4. A disposable tube according to claim 1 wherein:
   said first component is dry;
   said second component is a solvent for said component; and
   said solvent is drawn into said first compartment when said bellows is extended.

* * * * *